United States Patent
Trunet et al.

(10) Patent No.: US 11,918,679 B2
(45) Date of Patent: Mar. 5, 2024

(54) ACTIVE MIXURE

(71) Applicant: SYMRISE AG, Holzminden (DE)

(72) Inventors: Aurélie Trunet, Levallois Perret (FR); Caroline Baptiste, Paris (FR); Marielle Le Maire, Boulogne-Billancourt (FR)

(73) Assignee: Symrise AG, Holzminden (DE)

( * ) Notice: Subject to any disclaimer, the term of this patent is extended or adjusted under 35 U.S.C. 154(b) by 1113 days.

(21) Appl. No.: 16/088,659

(22) PCT Filed: Mar. 30, 2016

(86) PCT No.: PCT/EP2016/056977
§ 371 (c)(1),
(2) Date: Sep. 26, 2018

(87) PCT Pub. No.: WO2017/167364
PCT Pub. Date: Oct. 5, 2017

(65) Prior Publication Data
US 2023/0133290 A1     May 4, 2023

(51) Int. Cl.
| | |
|---|---|
| A61K 36/00 | (2006.01) |
| A61K 8/34 | (2006.01) |
| A61K 8/60 | (2006.01) |
| A61K 8/73 | (2006.01) |
| A61K 8/9794 | (2017.01) |
| A61Q 19/00 | (2006.01) |
| A61Q 19/08 | (2006.01) |

(52) U.S. Cl.
CPC .............. *A61K 8/735* (2013.01); *A61K 8/347* (2013.01); *A61K 8/60* (2013.01); *A61K 8/9794* (2017.08); *A61Q 19/004* (2013.01); *A61Q 19/08* (2013.01)

(58) Field of Classification Search
CPC ................................ A61Q 17/04; A61Q 19/08
See application file for complete search history.

(56) References Cited

U.S. PATENT DOCUMENTS

| | | | |
|---|---|---|---|
| 2012/0064182 A1* | 3/2012 | Gohla | A61Q 19/08 977/926 |
| 2012/0121673 A1 | 5/2012 | Susak et al. | |
| 2013/0122036 A1 | 5/2013 | Declercq et al. | |

FOREIGN PATENT DOCUMENTS

| | | | |
|---|---|---|---|
| CN | 102 846 514 A | | 1/2013 |
| CN | 104587518 A | * | 5/2015 |
| CN | 104 873 436 A | | 9/2015 |
| CN | 104 984 391 A | | 10/2015 |
| EP | 2 347 755 A2 | | 7/2011 |
| JP | 2013-053126 A | | 3/2013 |

OTHER PUBLICATIONS

Azadi et al, Comparing the effect of visceral fat and barley seed ash (*Hordeum vulgare* L) with silversulfadiazine on burn wound healing in rats. Jundishapur journal of natural pharmaceutical products, (Feb. 2015) vol. 10, No. 1, pp. e20670 (Year: 2015).*
Diaz-Gonzalez et al, Inhibition of deleterious chronic wound enzymes with plant polyphenols. Biocatalysis and Biotransformation (2012), vol. 30, No. 1, pp. 102-110 (Year: 2012).*
"Skin care facial mask with moisturizing, whitening and anti-wrinkle effects, and its preparation method," CA 163:389113, Chemical Abstracts Service, Columbus, Ohio, US; Sep. 2, 2015 & CN 104 873 436.
"Cosmetic sunscreen hydrogel containing tea polyphenols," CA 158:196259, Chemical Abstracts Service, Columbus, Ohio, US; Jan. 2, 2013 & CN 102 846 514.
"One kind of peripheral nerve repair membrane and preparation method thereof," CA 164:14315, Chemical Abstracts Service, Columbus, Ohio, US; Oct. 21, 2015 & CN 104 984 391.
"Skin external preparation, e.g. cream and milky lotion useful for preventing roughening and aging of skin, and masking wrinkles, comprises polyphenol mixture extracted from malt of barley," Abstract 2013-D93171, Database WPI—Thomson Scientific, London, GB; Mar. 21, 2013 & JP 2013-053126.

* cited by examiner

*Primary Examiner* — Qiuwen Mi
(74) *Attorney, Agent, or Firm* — Dilworth & Barrese, LLP

(57) ABSTRACT

Suggested is an active mixture, comprising or consisting of: (a) at least one biopolymer; (b) at least one glycosaminoglycan; (c) at least one disaccharide; and optionally (d) at least one active selected from the group consisting of phenols and/or polyphenols.

13 Claims, 6 Drawing Sheets

ACTIVE MIXTURE

FIELD OF INVENTION

The present invention belongs to the area of cosmetics and refers to a complex mixture for rejuvenating human skin, compositions comprising said mixture, a method for fighting skin ageing and the use of said mixture as an anti-ageing active.

STATE OF THE ART

How to rejuvenate human skin in 5 minutes? This a basic question for all producers of cosmetic products still looking for that magic "Cinderella" active that allows turning old, rough and floppy skin in the twinkling of an eye into young, smooth and firm tissue. In fact, fine lines and wrinkles are the main concern of women fighting signs of ageing. Studies show that 81% of female consumers that seek quick and visible results spend 70% more than average on face care. At the same time, 70% of these consumers want to know which ingredients their products contain, while products containing actives which are directly derived from natural sources, in particular from plants are by far preferred.

No doubt, state of the art provides a magnitude of alternatives how to solve the problem, which work, some better some worse. Various actives are cited again and again for solving the problem of everlasting young and pretty skin: caffeine, elastin, collagen, vitamin A, E, C, and in particular extracts forming an extraordinary botanical selection starting from A like Aronia to Z like Zao.

A major disadvantage of the products within the market is that they require a high number of applications over a long period of time in order to exhibit a visible and remarkable effect—if any.

Therefore, the problem underlying the present invention has not been simply to develop another cocktail of actives for rejuvenating skin, but to provide a composition that needs only a single application and leads within a couple of minutes to a visible tightening effect on skin.

DESCRIPTION OF THE INVENTION

Object of the present invention is an active mixture, comprising or consisting of:
(i) at least one biopolymer;
(ii) at least one glycosaminoglycan;
(iii) at least one disaccharide; and optionally
(iv) at least one active selected from the group consisting of phenols and/or polyphenols.

Surprisingly, it has been observed that the ternary and preferably the quaternary compositions when applied improve tension of human skin. In fact, skin becomes significantly smoother, the appearance of wrinkles and fine lines decreases. Most surprising has been that this effect does not require the application over days and weeks, but visible effects are achieved within 5 to 10 minutes as can be shown from objective data. The effect can be described as "natural photo shopping".

BRIEF DESCRIPTION OF THE DRAWINGS

The present invention will be described in greater detail with reference to the accompanying drawings, in which.

DETAILED DESCRIPTION OF THE INVENTION

Biopolymers

Figure 1A:
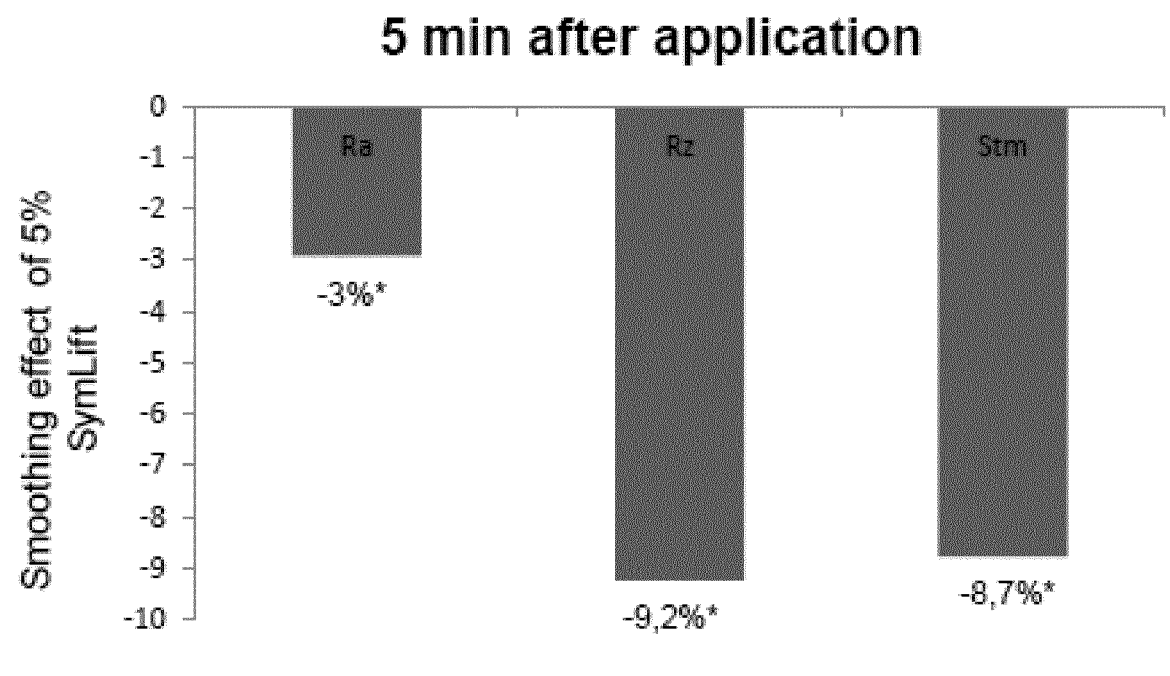
FIG. 1A is a graph documenting anti-wrinkle effect on crow's feet.

A biopolymer (component a) is a polymeric structure that is found in or is copied from nature. In the framework of the present invention this term is covered by beta-glucans on one side and chitosans on the other.

Beta Glucans

β-Glucans comprise a group of β-D-glucose polysaccharides naturally occurring in the cell walls of cereals, yeast, bacteria, and fungi, with significantly differing physicochemical properties dependent on source. Typically, β-glucans form a linear backbone with 1-3 β-glycosidic bonds but vary with respect to molecular mass, solubility, viscosity, branching structure, and gelation properties, causing diverse physiological effects in animals.

Various studies have examined the potential health effects of β-glucan. Oat fibre β-glucan at intake levels of at least 3 g per day can decrease the levels of saturated fats in the blood and may reduce the risk of heart disease. Some studies have suggested that cereal-derived β-glucan may also have immunomodulatory properties. Yeast and medicinal mushroom derived β-glucans have been investigated for their ability to modulate the immune system. β-glucans are further used in various nutraceutical and cosmetic products, as texturing agents, and as fibre supplements, but can be problematic in the process of brewing.

Glucans are arranged in six-sided D-glucose rings connected linearly at varying carbon positions depending on the source, although most commonly β-glucans include a 1-3 glycosidic link in their backbone. Although technically β-glucans are chains of D-glucose polysaccharides linked by 3-type glycosidic bonds, by convention not all 3-D-glucose polysaccharides are categorized as β-glucans. Cellulose is not typically considered a β-glucan, as it is insoluble and does not exhibit the same physicochemical properties as other cereal or yeast β-glucans.[4]

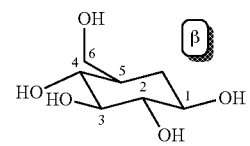

Some β-glucan molecules have branching glucose side-chains attached to other positions on the main D-glucose chain, which branch off the β-glucan backbone. In addition, these side-chains can be attached to other types of molecules, like proteins, as in Polysaccharide-K.

The most common forms of β-glucans are those comprising D-glucose units with β-1,3 links. Yeast and fungal β-glucans contain 1-6 side branches, while cereal β-glucans contain both β-1,3 and β-1,4 backbone bonds. The frequency, location, and length of the side-chains may play a role in immunomodulation. Differences in molecular weight, shape, and structure of β-glucans dictate the differences in biological activity.

β-glucans form a natural component of the cell walls of bacteria, fungi, yeast, and cereals such as oat and barley. Each type of beta-glucan comprises a different molecular backbone, level of branching, and molecular weight which is responsible for its solubility and physiological impact. One of the most common sources of β(1,3)D-glucan for supplement use is derived from the cell wall of baker's yeast (*Saccharomyces cerevisiae*). The β(1,3)D-glucans from yeast are often insoluble. However, β(1,3)(1,4)-glucans are also extracted from the bran of some grains, such as oats and barley, and to a much lesser degree in rye and wheat. Other sources include some types of seaweed,[8] and various species of mushrooms, such as reishi, *Ganoderma opplanatum*[9], shiitake, Chaga and maitake.

Cereal β-glucans from oat, barley, wheat, and rye, induce a variety of physiological effects that positively impact health. Barley and oat β-glucans have been studied for their effects on blood glucose regulation in test subjects with hypercholesterolemia Oats and barley differ in the ratio of trimer and tetramer 1-4 linkages. Barley has more 1-4 linkages with a degree of polymerization higher than 4. However, the majority of barley blocks remain trimers and tetramers. In oats, β-glucan is found mainly in the endosperm of the oat kernel, especially in the outer layers of that endosperm.

β-D-Glucan forms part of the cell wall of certain medically important fungi, especially *Aspergillus* and *Agaricus* species. Mushroom beta-glucans are linked by 1,3 glycosidic bonds with 1,6 branches. An assay to detect its presence in blood is marketed as a means of diagnosing invasive fungal infection in patients. False positives may occur because of fungal contaminants in the antibiotics amoxicillin-clavulanate, and piperacillin/tazobactam. False positives can also occur with contamination of clinical specimens with the bacteria *Streptococcus pneumoniae*, *Pseudomonas aeruginosa*, and *Alcaligenes faecalis*, which also produce (1→3)β-D-glucan.

Mushroom β-glucans have been proposed to act as "biological response modifiers" based on their effects on the immune system.[17] It has been suggested that receptors on the surface of innate immune cells called dectin-1 and complement receptor 3 (CR3 or CD11b/CD18) are responsible for binding to β-glucans, allowing the immune cells to recognize them as "non-self". This immune response regulation also affects antitumour properties. Several studies note an impact on epithelial cell cytokine generation.

β-Glucans found in the cell walls of yeast contain a 1,3 carbon backbone with elongated 1,6 carbon branches. A series of human clinical trials in the 1990s evaluated the impact of PGG-glucan on infections in high-risk surgical patients. In these studies, PGG-glucan significantly reduced complications. Orally administered yeast-glucan was reported to decrease the levels of IL-4 and IL-5 cytokines responsible for the clinical manifestation of allergic rhinitis, while increasing the levels of IL-12.

In the course of the present invention the most preferred beta-glucans are fractions from oat kernel.

Chitosans

Chitosans are biopolymers which belong to the group of hydrocolloids. Chemically, they are partly de-acetylated chitins differing in their molecular weights which contain the following—idealized—monomer unit:

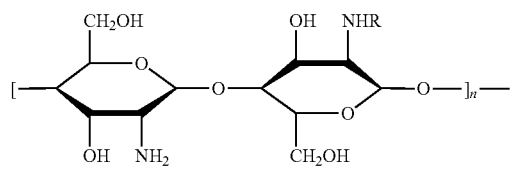

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations.

Glycosaminoglycans

Glycosaminoglycans (GAGs) also called mucopolysaccharides are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) orgalactose. Glycosaminoglycans are highly polar and attract water. They are therefore useful to the body as a lubricant or as a shock absorber.

Glycosaminoglycans have high degrees of heterogeneity with regards to molecular mass, disaccharide construction, and sulfation due to the fact that GAG synthesis, unlike proteins or nucleic acids, is not template driven, and dynamically modulated by processing enzymes.

Based on core disaccharide structures, GAGs are classified into four groups. Heparin/heparan sulfate (HSGAGs) and chondroitin sulfate/dermatan sulfate (CSGAGs) are synthesized in the Golgi apparatus, where protein cores made in the rough endoplasmic reticulum are posttranslationally modified with O-linked glycosylations by glycosyltransferases forming proteoglycans. Keratan sulfate may modify core proteins through N-linked glycosylation or O-linked glycosylation of the proteoglycan. The fourth class of GAG, hyaluronic acid, is not synthesized by the Golgi, but rather by integral membrane synthases which immediately secrete the dynamically elongated disaccharide chain.

HSGAG and CSGAG modified proteoglycans first begin with a consensus Ser-Gly/Ala-X-Gly motif in the core protein. Construction of a tetrasaccharide linker that consists of -GlcAβ1-3Galβ1-3Galβ1-4Xylβ1-O-(Ser)-, where xylosyltransferase, β4-galactosyl transferase (GalTI), β3-galactosyl transferase (GalT-II), and β3-GlcA transferase (GlcAT-I) transfer the four monosaccharides, begins synthesis of the GAG modified protein. The first modification of the tetrasaccharide linker determines whether the HSGAGs or CSGAGs will be added. Addition of a GlcNAc promotes the addition of HSGAGs while addition of GalNAc to the tetrasaccharide linker promotes CSGAG development.[5] GlcNAcT-I transfers GlcNAc to the tetrasaccharide linker, which is distinct from glycosyltransferase GlcNAcT-II, the enzyme that is utilized to build HSGAGs. Interestingly, EXTL2 and EXTL3, two genes in the EXT tumor suppressor family, have been shown to have GlcNAcT-I activity. Conversely, GalNAc is transferred to the linker by the enzyme GalNAcT to initiate synthesis of CSGAGs, an enzyme which may or may not have distinct activity compared to the GalNAc transferase activity of chondroitin synthase.

With regards to HSGAGs, a multimeric enzyme encoded by EXT1 and EXT2 of the EXT family of genes, transfers both GlcNAc and GlcA for HSGAG chain elongation. While elongating, the HSGAG is dynamically modified, first by N-deacetylase, N-sulfotransferase (NDST1), which is a bifunctional enzyme that cleaves the N-acetyl group from GlcNAc and subsequently sulfates the N-position. Next, C-5 uronyl epimerase coverts d-GlcA to I-IdoA followed by 2-O sulfation of the uronic acid sugar by 2-O sulfotransferase (Heparan sulfate 2-O-sulfotransferase). Finally, the 6-O and 3-O positions of GlcNAc moieties are sulfated by 6-O (Heparan sulfate 6-O-sulfotransferase) and 3-O (3-OST) sulfotransferases.

Chondroitin sulfate and dermatan sulfate, which comprise CSGAGs, are differentiated from each other by the presence of GlcA and IdoA epimers respectively. Similar to the production of HSGAGs, C-5 uronyl epimerase converts d-GlcA to I-IdoA to synthesize dermatan sulfate. Three sulfation events of the CSGAG chains occur: 4-O and/or 6-O sulfation of GalNAc and 2-O sulfation of uronic acid. Four isoforms of the 4-O GalNAc sulfotransferases (C4ST-1, C4ST-2, C4ST-3, and D4ST-1) and three isoforms of the GalNAc 6-O sulfotransferases (C6ST, C6ST-2, and GalNAc4S-6ST) are responsible for the sulfation of GalNAc.

Unlike HSGAGs and CSGAGs, the third class of GAGs, those belonging to keratan sulfate types, are driven towards biosynthesis through particular protein sequence motifs. For example, in the cornea and cartilage, the keratan sulfate domain of aggrecan consists of a series of tandemly repeated hexapeptides with a consensus sequence of E(E/L)PFPS. Additionally, for three other keratan sulfated proteoglycans, umican, keratocan, and mimecan (OGN), the consensus sequence NX(T/S) along with protein secondary structure was determined to be involved in N-linked oligosaccharide extension with keratan sulfate. Keratan sulfate elongation begins at the nonreducing ends of three linkage oligosaccharides, which define the three classes of keratan sulfate. Keratan sulfate I (KSI) is N-linked via a high mannose type precursor oligosaccharide. Keratan sulfate II (KSII) and keratan sulfate III (KSIII) are O-linked, with KSII linkages identical to that of mucin core structure, and KSIII linked to a 2-O mannose. Elongation of the keratan sulfate polymer occurs through the glycosyltransferase addition of Gal and GlcNAc. Galactose addition occurs primarily through the β-1,4-galactosyltransferase enzyme (β4Gal-T1) while the enzymes responsible for β-3-Nacetylglucosamine have not been clearly identified. Finally, sulfation of the polymer occurs at the 6-position of both sugar residues. The enzyme KS-Gal6ST (CHST1) transfers sulfate groups to galactose while N-acetylglucosaminyl-6-sulfotransferase (GlcNAc6ST) (CHST2) transfers sulfate groups to terminal GlcNAc in keratan sulfate.

The fourth class of GAG, hyaluronan (or hyaluronic acid), is not sulfated and is synthesized by three transmembrane synthase proteins HAS1, HAS2, and HAS3. HA, a linear polysaccharide, is composed of repeating disaccharide units of →4)GlcAβ(1→3)GlcNAcβ(1→ and has a very high molecular mass, ranging from $10^5$ to $10^7$ Da. Each HAS enzyme is capable of transglycosylation when supplied with UDP-GlcA and UDP-GlcNAc. HAS2 is responsible for very large hyaluronic acid polymers, while smaller sizes of HA are synthesized by HAS1 and HAS3. While each HAS isoform catalyzes the same biosynthetic reaction, each HAS isoform is independently active. HAS isoforms have also been shown to have differing $K_m$ values for UDP-GlcA and UD-PGlcNAc. It is believed that through differences in enzyme activity and expression, the wide spectrum of biological functions mediated by HA can be regulated.

While glycosaminoglycans (component b) can be selected from the group consisting of chondroitin sulfate, dermatan sulfate, keratin sulfate, heparin, heparin sulfate and hyaluronan or their mixtures, the most preferred one is hyaluronan (hyaluronic acid) or one of its salts (i. e. sodium hyaluronate).

Disaccharides

Disaccharides, forming component (c) represent sugars formed when two monosaccharides (simple sugars) are joined. Like monosaccharides, disaccharides are soluble in water. Three common examples are sucrose, lactose, and maltose. Disaccharides are one of the four chemical groupings of carbohydrates (monosaccharides, disaccharides, oligosaccharides, and polysaccharides). The most common types of disaccharides—sucrose, lactose, and maltose— have twelve carbon atoms, with the general formula $C_{12}H_{22}O_{11}$. The differences in the disaccharides are due to atomic arrangements within the molecule.

The joining of simple sugars into a double sugar happens by a condensation reaction, which involves the elimination of a water molecule from the functional groups only. Breaking apart a double sugar into its two simple sugars is accomplished by hydrolysis with the help of a type of enzyme called a disaccharidase. As building the larger sugar ejects a water molecule, breaking it down consumes a water molecule. These reactions are vital in metabolism. Each disaccharide is broken down with the help of a corresponding disaccharidase (sucrase, lactase, and maltase).

There are two different types of disaccharides:
Reducing disaccharides, in which one monosaccharide, the reducing sugar, still has a free hemiacetal unit; and non-reducing disaccharides, in which the components bond through an acetal linkage between their anomeric centres and neither monosaccharide has a free hemiacetal unit. Cellobiose and maltose are examples of reducing disaccharides.

Sucrose and trehalose are examples of non-reducing disaccharides.

The glycosidic bond can be formed between any hydroxyl group on the component monosaccharide. So, even if both component sugars are the same (e.g., glucose), different bond combinations (regiochemistry) and stereochemistry (alpha- or beta-) result in disaccharides that are diastereoisomers with different chemical and physical properties.

Depending on the monosaccharide constituents, disaccharides are sometimes crystalline, sometimes water-soluble, and sometimes sweet-tasting and sticky-feeling.

| Disaccharide | Unit 1 | Unit 2 | Bond |
|---|---|---|---|
| Sucrose (table sugar, cane sugar, beet sugar, or saccharose) | Glucose | Fructose | α(1→2)β |
| Lactulose | Galactose | Fructose | β(1→4) |
| Lactose (milk sugar) | Galactose | Glucose | β(1→4) |
| Maltose (malt sugar) | Glucose | Glucose | α(1→4) |
| Trehalose | Glucose | Glucose | α(1→1)α |
| Cellobiose | Glucose | Glucose | β(1→4) |
| Chitobiose | Glucosamine | Glucosamine | β(1→4) |

While said disaccharides can be selected from the group consisting of sucrose, lactulose, lactose, maltose, cellobiose, chitobiose, trehalose and mixtures thereof, the preferred species, however, is trehalose.

Actives

While the ternary mixtures explained above provide good results in terms of anti-ageing, it is a seriously preferred embodiment of the present invention to add actives selected from the group consisting of caffeic acid (I), coumaric acid (II), ferulic acid (III), diferulic acids (IV), saponarins (V), catechins (VI), procyanidins (VII), prodelphinidins (VIII), hordenine (IX) and mixtures thereof as component (d).
Caffeic acid (I)
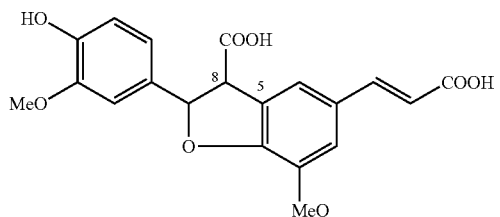
p-Coumaric acid (II)
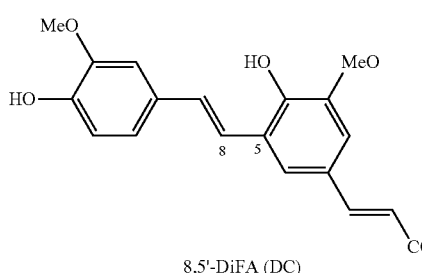
Ferulic acid (III)
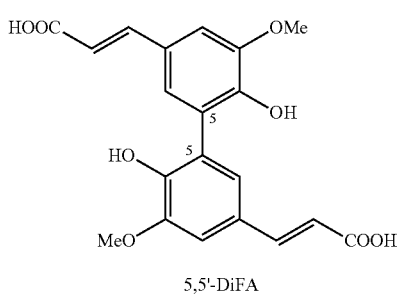
8,8'-DiFA
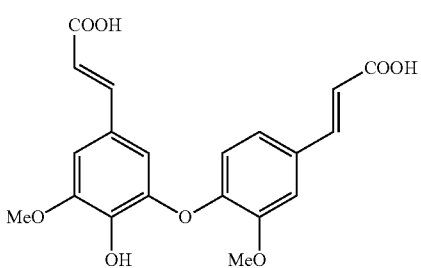
8,8'-DiFA (THF;
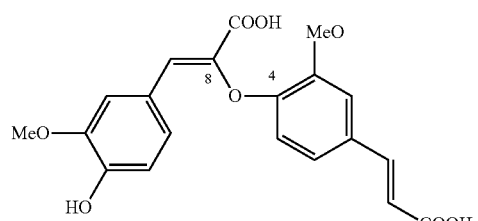
8,8'-DiFA (AT)
8,5'-DiFA
-continued
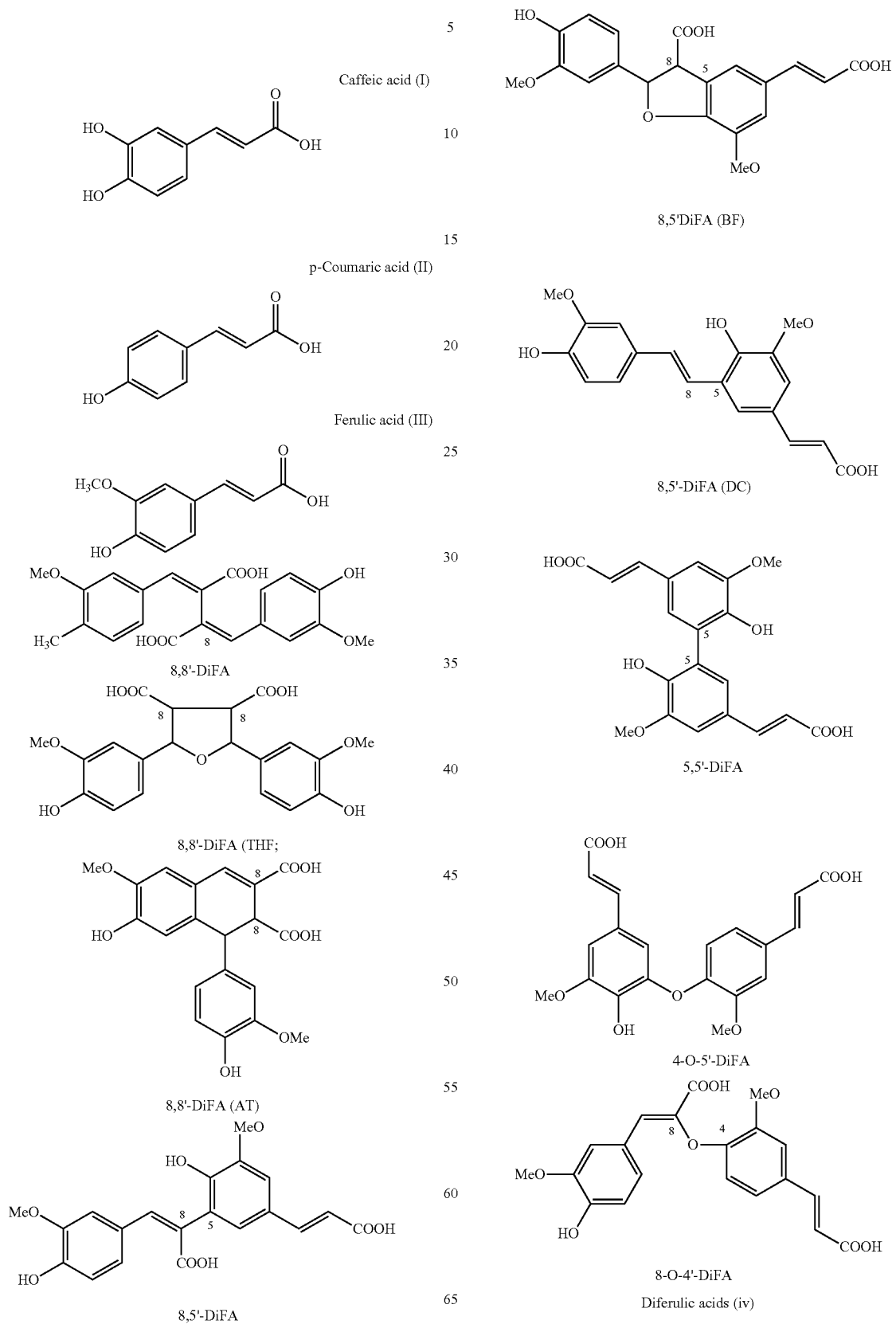
8,5'DiFA (BF)
8,5'-DiFA (DC)
5,5'-DiFA
4-O-5'-DiFA
8-O-4'-DiFA
Diferulic acids (iv)

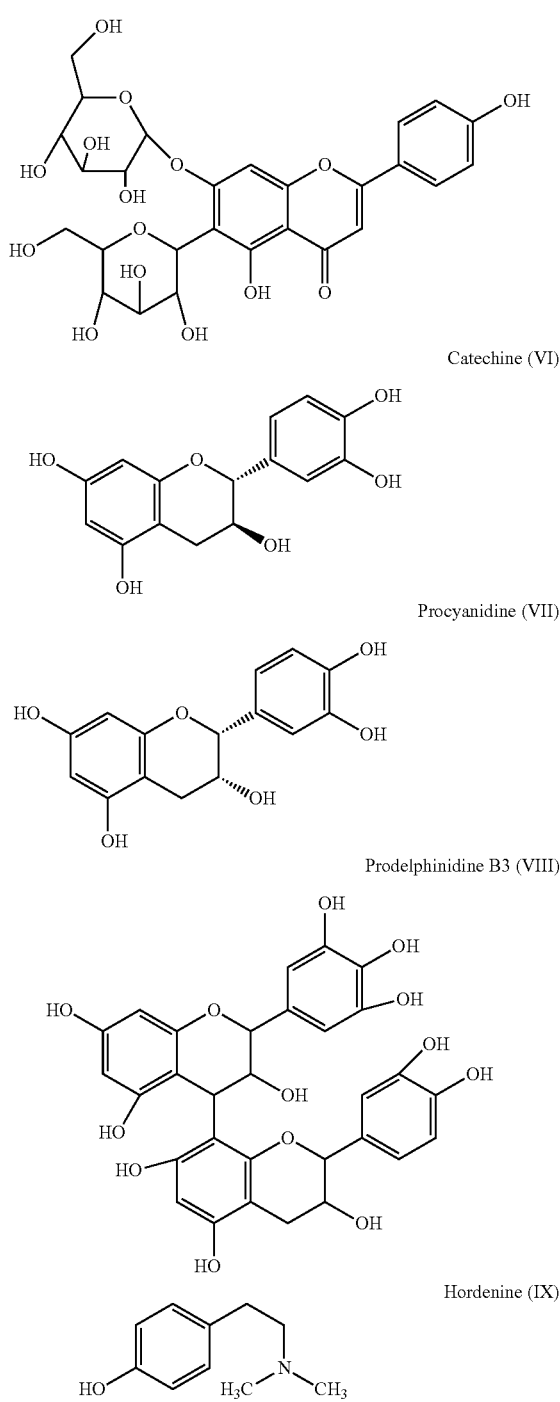

Saponarine (V)

Catechine (VI)

Procyanidine (VII)

Prodelphinidine B3 (VIII)

Hordenine (IX)

The mixtures according to the present invention may comprise one, two, three or even all of the actives (I) to (IX) including similar species, like gallocatechines, epigallocatechines and the like.

An overall preferred embodiment, however, is to add as component (d) an extract of *Hordeum vulgare* (barley) to the composition, since these extracts contain almost all or even all actives cited above in working amounts.

Carriers

The mixtures comprising components (a), (b), (c) and optionally (d) may be blended with a carrier which is cosmetically acceptable. Examples for suitable carriers encompass water, $C_2$-$C_4$ aliphatic alcohols, $C_2$-$C_4$ alkylene glycols, $C_6$-$C_{12}$ alkanediols, glycerol, oil bodies and their mixtures. Preferred carriers are water, glycerol, alkanediols like for example 1,2-hexanediol, and/or glycols like for example pentylene glycol, caprylyl glycol or mixtures thereof.

Typically the amount of carriers in the blend ranges from about 99 to about 50% b.w., preferably about 90 to about 70% b.w. and particularly from about 85 to about 75% b.w.

Mixtures

In a preferred embodiment of the present invention the mixtures comprise or consist of:
(a) about 10 to about 40% b.w., preferably about 15 to about 35% b.w., and even more preferred about 20 to about 30% b.w. of at least one biopolymer;
(b) about 1 to about 15% b.w., preferably about 2 to about 12% b.w., and even more preferred about 5 to about 10% b.w. of at least one glycosaminoglycan;
(c) about 10 to about 40% b.w., preferably about 15 to about 35% b.w., and even more preferred about 20 to about 30% b.w. of at least one disaccharide; and optionally
(d) 0 to about 5% b.w., preferably about 0.5 to about 4% b.w., and even more preferred about 1 to about 2% b.w. of at least one active selected from the group consisting of phenols and/or polyphenols,
on condition that the amounts add—optionally with a cosmetically acceptable carrier—to 100% b.w.

Another preferred embodiment of the invention refers to mixtures comprising or consisting of:
(a) about 1 to about 15% b.w., preferably about 2 to about 12% b.w., and even more preferred about 5 to about 10% b.w beta-glucan(s);
(b) about 1 to about 15% b.w., preferably about 2 to about 12% b.w., and even more preferred about 5 to about 10% b.w.
(c) about 10 to about 40% b.w., preferably about 15 to about 35% b.w., and even more preferred about 20 to about 30% b.w. of D-trehalose; and
(d) 0 to about 5% b.w., preferably about 0.5 to about 4% b.w., and even more preferred about 1 to about 2% b.w. extract of *Hordeum vulgare*,
on condition that the amounts add—optionally with a cosmetically acceptable carrier—to 100% b.w.

Cosmetic Compositions

Another object of the present invention refers to cosmetic compositions comprising the above-references active mixture. The term "cosmetic composition" shall also encompass personal care compositions. Preferably, the active mixtures are present in said compositions in amounts of from about 0.1 to about 15% b.w., preferably about 1 to about 12% b.w. and even more preferred about 5 to about 10% b.w.

Said cosmetic or personal care composition preferably represents a skin care and/or sun care product, such as for example a cosmetic cream, lotion, spray, emulsion, ointment, gel or mouse and the like. Typical examples are skin creams and sun care lotions.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

The same oil bodies can also be used as carriers for the mixtures according to the present invention.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens®

[Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (UvasoreHEB)
benzylidene malonate polysiloxane (Parsol®SLX)
glyceryl ethylhexanoate dimethoxycinnamate
dipropylene glycol salicylate
tris(2-ethylhexyl)-4,4',4''-(1,3,5-triazine-2,4,6-triyl-triimino)tribenzoate (=2,4,6-trianilino(p-carbo-2'-ethylhexyl-1'-oxy)-1,3,5-triazine) (Uvinul®T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
2,2'-methylene bis-(6-(2H-benzotriazol-2-yl)-4-1,1,3,3-tetramethylbutyl) phenol) (Tinosorb®M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2''-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2''-methylpropyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/ (Neo Heliopan®357)
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene) methyl]benzyl] acrylamide polymer
p-methoxycinnamic acid-2-ethylhexyl ester (Neo Heliopan®AV)

p-aminobenzoic acid ethyl ester (25 mol) ethoxylated (INCI name: PEG-25 PABA)

p-methoxycinnamic acid isoamyl ester (Neo Heliopan®1000)

2,4,6-trianilino-(p-carbo-2'-ethylhexyl-1'-oxy)-1,3,5-triazine (Uvinul®T150)

phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan®MBC)

3-benzylidene camphor salicylic acid-2-ethylhexyl ester (Neo Heliopan®OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine (Tinosorb®S)

benzylidene malonate polysiloxane (Parsol®SLX)

menthyl anthranilate (Neo Heliopan®MA)

2-(4-diethylamino-2-hydroxybenzoyl) benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin Pigmentation

Preferred active ingredients for skin lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Additional Anti-Ageing Actives

In the context of the invention, further anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and additional plant extracts.

Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *Sophora*, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Glycosaminoglycan stimulators. Preferred compositions comprise substances stimulating the synthesis of glycosaminoglycans selected from the group consisting of hyaluronic acid and derivatives or salts, Subliskin (Sederma, INCI: *Sinorhizobium meliloti* Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (-)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (-)alpha-bisabolol or synthetic alpha-bisabolol such as e.g. Dragosantol and Dragosantol 100 from Symrise, oat glucan, *Echinacea purpurea* extract, *Sinorhizobium meliloti* Ferment Filtrate, Calcium ketogluconate, Alpinia galanga leaf extract and tetradecyl aminobutyroylvalylaminobutyric urea trifluoroacetate.

Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*; preferably selected from the group consisting of extracts or fractions from camomile, Aloe vera, oats, calendula, arnica, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-) ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as 3-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodes-mosomes, glycosidases, stratum corneum chymotryptic enzyme (SCCE) or other proteaces (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N ethane)sulphonic acid (HEPES), 3-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-cellulite agents. Anti-cellulite agents and lipolytic agents are preferably selected from the group consisting of those described in WO 2007/077541, and beta-adrenergic receptor agonists such as Synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzym A, isoflavonoides, soy extracts, ananas extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof, the semiesters of menthols with a dicarboxylic acid or derivatives thereof (for example monomenthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8- diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Inflammatory Agents

Suitable anti-inflammatory agents may be selected from the group formed by:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone,
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone,
(iii) natural or naturally occurring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof,
(iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ⍺-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, clovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

Another object of the present invention refers to a method for improving skin tension encompassing the following steps:
(i) providing the mixture comprising compounds (a), (b) (c) and optionally (d); and
(ii) applying said mixture to human skin,
preferably over a period of about 5 to about 10 minutes.

Finally, the invention also encompasses the use of the mixtures for improving tension of skin, including soothing the skin, reducing deepness and number of wrinkles and an overall rejuvenation of the skin, preferably within a very short of 5 to 10 minutes after application.

With regard to preferred embodiments, preferred combinations, relations and amounts reference is made to the disclosure above which apply for the respective process and use mutatis-mutandis; a repetition is therefore not necessary.

EXAMPLES

Example 1

Wrinkle and Fine Lines Reduction Measurements

The following examples are conducted by a mixture consisting of the compositions as exhibited in Table 1:

TABLE 1

| Component | Active mixture | | | | |
| --- | --- | --- | --- | --- | --- |
| | A | B | C | D | E |
| Beta-glucan | 1.0 | — | 0.5 | 2.0 | 5.0 |
| Chitosan | — | 1.0 | — | — | — |
| Hyaluronic acid | 0.5 | 0.5 | 1.0 | 0.5 | 1.0 |
| D-Trehalose | 5.0 | 4.0 | 3.0 | 2.0 | 1.0 |
| Barley extract | 0.5 | 1.0 | 0.5 | 0.5 | — |
| Carrier* | Ad to 100% | | | | |

*Aqueous mixture comprising glycerin, pentylene glycol, 1,2-hexanediol and caprylyl glycol.

Protocol

A skin's micro-relief and wrinkle profile was evaluated using 3 dimensional DermaTop® software for detection of skin cutaneous parameters after 5 min. The composition according to Example A diluted at 5% in water was applied on 21 panellists aged between 45-55 years old and having wrinkles of grades 2 & 3 (medium grade). The application of the placebo (water) and the test mixture was randomized and standardized by a technician on crow's feet area.

Studied Parameters

Ra: the average roughness (in μm): a decrease in this parameter characterizes a smoothing effect (first column)

Rz: the average relief: average of all picks-to-valley heights (second column)

Stm: volume measurement: mean of the maximum surface height difference—A decrease in one of these parameters (Stm and Rz) characterizes an anti-wrinkle effect of the product (third column)

Figures 1B, 1C:
FIGS. 1B and 1C are photographs showing decrease in skin roughness and wrinkling after application.

The results are shown in FIG. 1. FIG. 1A shows the anti-wrinkle effect on crow's feet. FIGS. 1B and 1C provide photos from a volunteer before and 5 minutes after the application. As one can see after 5 minutes of application a significant and visible decrease of skin roughness and wrinkles appears.

Figure 2A:
FIGS. 2A and 2B are high resolution photographs showing improved skin smoothness after application, FIG. 3 graphically illustrates a sensory evaluation profile of panelists having applied the active mixture of the invention to skin, and FIGS. 4A, 4B, and 4C graphically illustrate sensory evaluation profiles of panelists having applied different products according to the invention to skin.
Figure 2B:

FIG. 2 shows illustrative high resolution photography before (2A) and 5 minutes after application (2B). As one can see the skin is visibly smoother.

Figure 3:
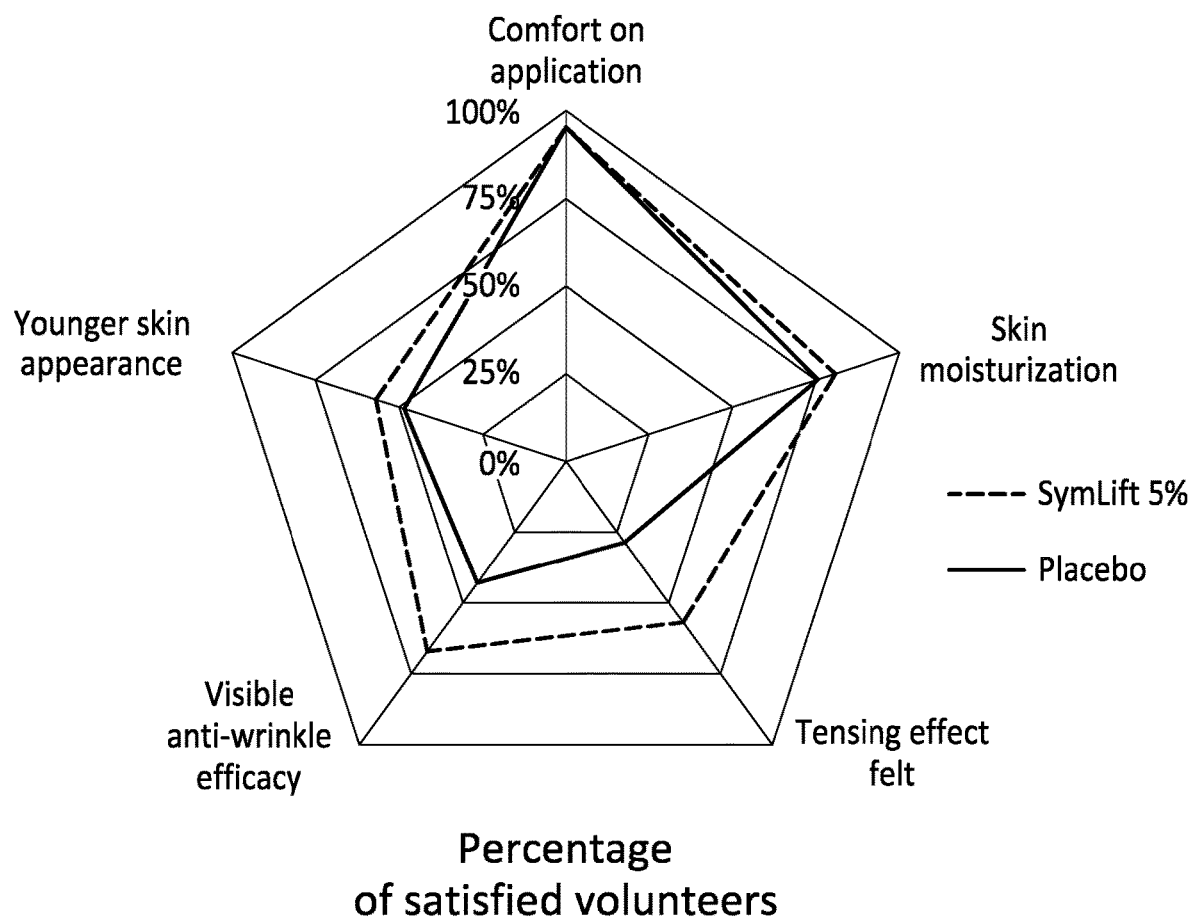

67% of the 21 panellists felt that their skin was smoother and fine lines and wrinkles appeared to be less deep. A tensing effect was confirmed by 57% of the panellists. A sensory profile as confirmed by the panellists is provided in FIG. 3. SYMLIFT™ stands for the mixture of Example A.

Example 2

Sensory Evaluation

The mixture according to Example A was applied at 10% to the skin of 16 expert panellists and the improvement of softness and spreadability was evaluated on a scale from (0)=not to be detected to (10)=very high. The results are provided in Table 2; a significant statistical test is $p<0.05$.

TABLE 2

Sensory evaluation of Mixture A

|  | Mixture A | Placebo |
|---|---|---|
| Softness | 7.2 | 5.5 |
| Spreadability | 9.1 | 8.8 |

Formulation Example F1

Visible and Instant Anti-Wrinkle Roll-on Composition (Amounts in % b.w.)

| Phase | Compound | INCI | Amount |
|---|---|---|---|
| A | WATER | AQUA | Ad 100 |
| A | SYMSAVE ® H | HYDROXYACETOPHENONE | 0.50 |
| B | KELTROL ® CG-T | XANTHAN GUM | 0.15 |
| B | HYDROLITE ® S | PENTYLENE GLYCOL | 2.00 |
| C | SYMLIFT ™ | AQUA TREHALOSE GLYCERIN PENTYLENE GLYCOL BETA-GLUCAN HORDEUM VULGARE SEED EXTRACT SODIUM HYALURONATE 1,2-HEXANEDIOL CAPRYLYL GLYCOL | 5.00 |
| D | SOLUBILIZER | PEG-40 HYDROGENATED CASTOR OIL TRIDECETH-9 PROPYLENE GLYCOL AQUA | 1.50 |
| E | FRESCOLAT ® X-COOL | MENTHYL ETHYLAMIDO OXALATE | 0.20 |

Production Method

Figure 4A:
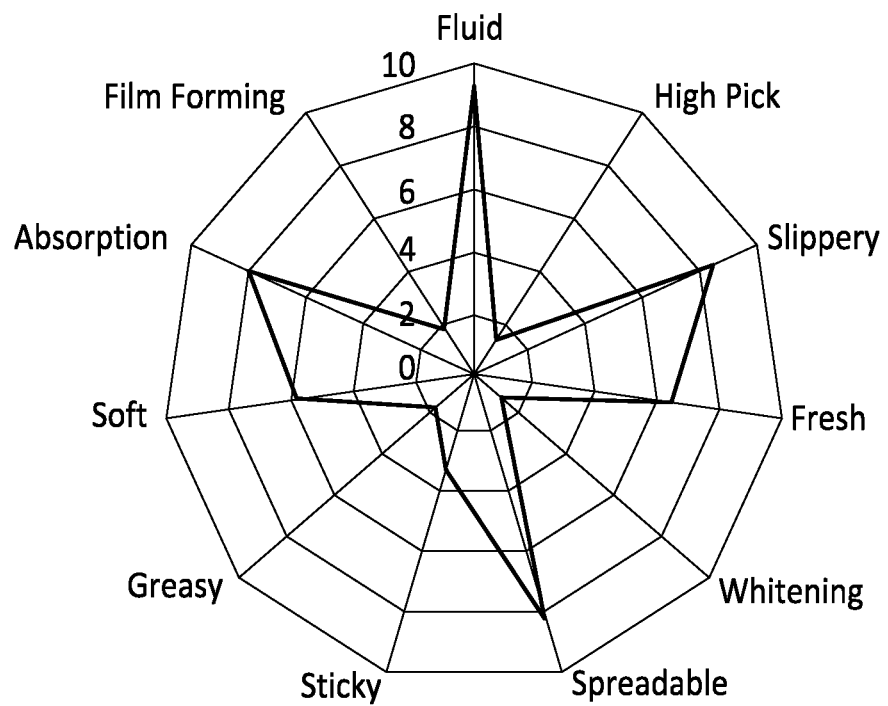

Dissolve SymSave® H in water while heating up to 40-50° C., then disperse Xanthan gum in Hydrolite® 5, and add to the batch while stirring, until homogeneous. Add ingredient of phase C and then add phase D, while stirring. Check pH is around 5.5. The sensory evaluation of the product is depicted in FIG. 4A.

Formulation Example F2

Anti-Ageing Serum (Amounts in % b.w.)

| Phase | Compound | INCI | Amount |
|---|---|---|---|
| A | DRACORIN ® GOC | GLYCERYL OLEATE CITRATE CAPRYLIC/CAPRIC TRIGLYCERIDE | 2.50 |
| A | PLC-LIQUID ®100 | CETEARYL ETHYLHEXANOATE | 2.50 |
|  | ISODRAGOL ® | TRIISONONANOIN | 4.00 |
|  | SYMMOLLIENT ® S | CETEARYL NONANOATE | 1.50 |
| A | XIAMETER ® PMX-200 SILICONE FLUID | DIMETHICONE | 1.00 |
|  | TOCOPHERYL ACETATE | TOCOPHEYL ACETATE | 0.10 |
| B | CARBOPOL ® ETD 2020 POLYMER | ACRYLATES/10-30 ALKYL ACRYLATE CROSSPOLYMER | 0.15 |
|  | KELTROL ® CG-T | XANTHAN GUM | 0.25 |
| C | WATER | AQUE | Ad 100 |
|  | SYMSAVE ® H | HYDROXYACETOPHENONE | 0.80 |
|  | SYMDIOL ® 68 | 1,2-HEXANEDIOL CAPRYLYL GLYCOL | 0.50 |
| D | SODIUM HYDROXIDE | AQUA SODIUM HYDROXIDE | 0.20 |
| E | SIMULGEN ® NS | HYDROXYETHYL ACRYLATE/SODIUM ACRYLOYL DIMETHYL TAURATE COPOLYMER | 0.60 |

| Phase | Compound | INCI | Amount |
|---|---|---|---|
| F | HYDROVITONE ® PLUS | SQUALANE<br>POLYSORBATE 60<br>AQUA<br>PENTYLENE GLYCOL<br>GLYCERIN<br>FRUCTOSE<br>UREA<br>CITRIC ACID<br>SODIUM HYDROXIDE<br>MALTOSE<br>SODIUM PCA<br>SODIUM CHLORIDE<br>SODIUM LACTATE<br>TREHALOSE<br>ALLANTOIN<br>SODIUM HYALURONATE<br>GLUCOSE | 2.00 |
| | SYMLIFT ™ | AQUA<br>TREHALOSE<br>GLYCERIN<br>PENTYLENE GLYCOL<br>BETA-GLUCAN<br>HORDEUM VULGARE SEED EXTRACT<br>SODIUM HYALURONATE<br>1,2-HEXANEDIOL<br>CAPRYLYL GLYCOL | 5.0 |
| | SYMFINITY ® | ECHINACEAE PURPURAE EXTRACT | 0.10 |
| G | FRAGRANCE | PARFUM | 0.30 |

Production Method

Figure 4B:
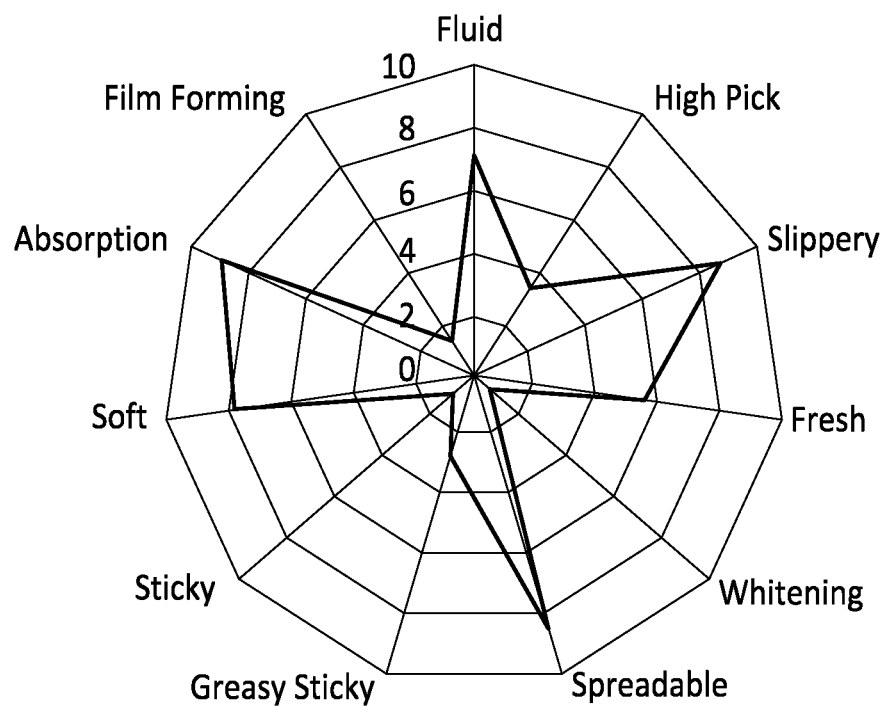

Heat phase A and phase C to 60° C. Disperse phase B into phase A under high shear and add phase C into phase A+B under high shear. Neutralize with sodium hydroxide, and add Simulgel NS. Homogenise with Ultra turrax. Let to cool down to 40° C. with gentle stirring, and add ingredients of phase F one by one under stirring and then phase G. Check pH is around 5. Viscosity: 401 cP Spindle: 21/Speed (RPM): 100/T(° C.): 19.2° C./Torque (%): 80.3%/S STR: 372.9 (D/cm$^2$)/S RATE: 93 (s-1) The sensory evaluation of the product is depicted in FIG. 4B.

Formulation Example F3

Silky Lifting Spray (Amounts in % b.w.)

| Phase | Compound | INCI | Amount |
|---|---|---|---|
| A | DRACORIN ® GOC | GLYCERYL OLEATE CITRATE | 2.00 |
| A | PLC-LIQUID ®100 | CAPRYLIC/CAPRIC TRIGLYCERIDE<br>CETEARYL ETHYLHEXANOATE | 4.00 |
| B | SYMMOLLIENT ® S | CETEARYL NONANOATE | 1.50 |
| | DRAGOXAT 89 | Ethylhexyl isononanoate | 6.00 |
| | XIAMETER ® PMX-200 SILICONE FLUID | DIMETHICONE | 8.00 |
| | TOCOPHERYL ACETATE | TOCOPHERYLACETATE | 0.20 |
| | SYM3D | PROPYLMETHYLMETHOXYBENZOFURAN | 0.25 |
| | SYMLIFT ™ | AQUA<br>TREHALOSE<br>GLYCERIN<br>PENTYLENE GLYCOL<br>BETA-GLUCAN<br>HORDEUM VULGARE SEED EXTRACT<br>SODIUM HYALURONATE<br>1,2-HEXANEDIOL<br>CAPRYLYL GLYCOL | 10.0 |
| | KELTROL ® CG-T | XANTHAN GUM | 0.25 |
| B | PEMULEN TR-2 | ACRYLATES/C10-30 ALKYL ACRYLATE CROSSPOLYMER | 0.15 |
| C | POLYMERIC EMULSIFIER WATER | AQUA | Ad 100 |
| C | GLYCERIN | GLYCERIN | 2.0 |
| | HYDROLITE 5 | PENTYLENE GLYCOL | 2.00 |
| C | SYMOCIDE PS | PHENOXYETHANOL<br>DECYLENE GLYCOL<br>1,2-HEXANEDIOL | 0.60 |
| D | SODIUM HYDROXIDE | SODIUM HYDROXIDE | 0.30 |
| E | FLAMENCO SUMMIT GOLD y30D | MICA TITANIUM DIOXIDE | 0.30 |
| | FRAGRANCE | PARFUM | 0.50 |

Production Method

Phase A: Blend ingredients and heat slightly to 45° C. until SymMollient® S and Sym3D° are melted.

Phase C: Blend ingredients while stirring.

Figure 4C:
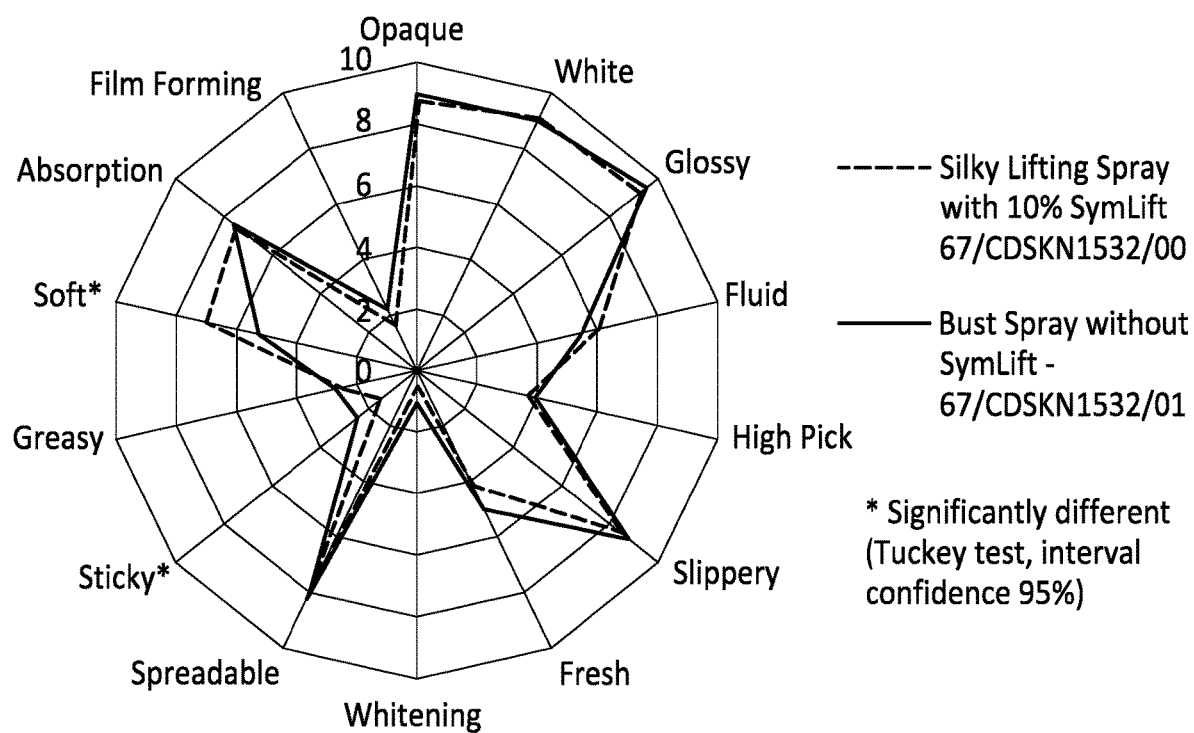

Disperse phase B into phase A under high shear and add phase C into A+B under high shear. Add phase D&E successively under stirring and check pH is 5.5 pH: 5.7, Viscosity: 335.7 cP, Spindle: 21/Speed (RPM): 120/T(° C.): 21° C./Torque (%): 80.6%/S STR: 373.9 (D/cm$^2$)/S RATE: 112 (s-1) The sensory evaluation of the product is depicted in FIG. 4C.

The invention claimed is:

1. An active mixture, comprising:
   (a) about 10 to about 40% b.w. of at least one biopolymer;
   (b) about 1 to about 15% b.w. of at least one glycosaminoglycan;
   (c) about 10 to about 40% b.w. of at least one disaccharide; and
   (d) about 0.5 to about 5% b.w. of an extract of *Hordeum vulgare*,
   with all amounts of (A)-(d) adding, optionally with a cosmetically acceptable carrier, to 100% b.w., and
   wherein said biopolymer (a) is either a beta-glucan or a mixture of beta-glucan and chitosan.

2. The mixture of claim 1, wherein said glycosaminoglycan is selected from the group consisting of chondroitin sulfate, dermatan sulfate, keratin sulfate, heparin, heparin sulfate, hyaluronic acid, and mixtures thereof.

3. The mixture of claim 1, wherein said disaccharide is selected from the group consisting of sucrose, lactulose, lactose, maltose, cellobiose, chitobiose, trehalose, and mixtures thereof.

4. The mixture of claim 1, wherein said extract of *Hordeum vulgare* includes an active selected from the group consisting of caffeic acid, coumaric acid, ferulic acid, diferulic acid, saponarins, catechins, procyanidins, prodelphinidins, hordenine, and mixtures thereof.

5. The mixture of claim 1, further comprising a cosmetically acceptable carrier.

6. The mixture of claim 5, wherein said carrier is selected from the group consisting of water, $C_2$-$C_4$ aliphatic alcohols, $C_2$-$C_4$ alkylene glycols, $C_6$-$C_{12}$ alkanediols, glycerol, oil bodies, and mixtures thereof.

7. The mixture of claim 1, comprising
   (a) about 10 to about 40% b.w. beta-glucan(s);
   (b) about 1 to about 15% b.w. hyaluronic acid;
   (c) about 5 to about 45% b.w. D-trehalose; and
   (d) about 1 to about 2% b.w. extract of *Hordeum vulgare*,
   with all amounts of (a)-(d) adding optionally with a cosmetically acceptable carrier, to 100% b.w.

8. A cosmetic composition comprising the mixture of claim 1.

9. The composition of claim 8, comprising the mixture in an amount of from about 0.1 to about 10% b.w.

10. The composition of claim 8, being a skin care and/or sun care composition.

11. The mixture of claim 1, comprising an amount effective for improving tension of skin.

12. An active mixture, consisting of:
    (a) about 10 to about 40% b.w. of at least one biopolymer;
    (b) about 1 to about 15% b.w. of at least one glycosaminoglycan;
    (c) about 10 to about 40% b.w. of at least one disaccharide; and optionally
    (d) about 0.5 to about 5% b.w. of at least one active selected from the group consisting of phenols, polyphenols, and mixtures thereof, with all amounts of (a)-(c), and optionally component (d), adding with a cosmetically acceptable carrier to 100% b.w., and
    wherein said biopolymer forming group (a) is either at least one beta-glucan or a mixture of at least one beta-glucan and at least one chitosan.

13. A method for improving tension of skin comprising the steps of:
    (i) providing the mixture of claim 1; and
    (ii) applying said mixture to human skin.

* * * * *